(12) United States Patent
Mandava et al.

(10) Patent No.: US 8,013,181 B2
(45) Date of Patent: Sep. 6, 2011

(54) PREPARATION OF RIVASTIGMINE AND ITS SALTS

(75) Inventors: Venkata Naga Brahmeswara Rao Mandava, Hyderabad (IN); Venkata Reddy Vajrala, Hyderabad (IN); Ganesh Varanasi, Hyderabad (IN); Vijay Kumar Adla, Warangal (IN); Mukund Reddy Jambula, Hyderabad (IN); Vijaypal Reddy Kanumathi Reddy, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 634 days.

(21) Appl. No.: 12/100,591

(22) Filed: Apr. 10, 2008

(65) Prior Publication Data

US 2008/0255383 A1 Oct. 16, 2008

Related U.S. Application Data

(60) Provisional application No. 61/030,814, filed on Feb. 22, 2008.

(30) Foreign Application Priority Data

Apr. 10, 2007 (IN) .............................. 758/CHE/2007

(51) Int. Cl.
*C07C 269/00* (2006.01)

(52) U.S. Cl. ..................................................... 560/136
(58) Field of Classification Search .................. None
See application file for complete search history.

(56) References Cited

U.S. PATENT DOCUMENTS

| 4,948,807 | A | 8/1990 | Rosin et al. | |
|---|---|---|---|---|
| 5,602,176 | A | 2/1997 | Enz | |
| 6,333,358 | B1 * | 12/2001 | Nakazato et al. | 514/650 |

FOREIGN PATENT DOCUMENTS

| EP | 0193926 B1 | 11/1990 |
|---|---|---|
| WO | 9602492 A1 | 2/1996 |
| WO | 2004/037771 A1 | 5/2004 |
| WO | 2005/058804 A1 | 6/2005 |

OTHER PUBLICATIONS

Zhou et al, Zhongguo Yiyao Gongye Zazhi, Synthesis of N-Ethyl-N-methylcarbamic Acid 3-[(1S)-1-(dimethylamino)ethyl]phenyl Ester, (2R,3R)-2,3-dihydroxybutanedioate (Rivastigmine Hydrogen Tartrate), 2007, 38(5), pp. 327-329, Abstract and CAS record.*

* cited by examiner

*Primary Examiner* — Paul A Zucker
(74) *Attorney, Agent, or Firm* — Thomas C. McKenzie; Balaram Gupta; Robert A. Franks

(57) ABSTRACT

There are provided processes for making rivastigmine. In one embodiment, the process includes reacting S-(−)-[1-(3-hydroxyphenyl)ethyl]dimethylamine with N-ethyl-N-methyl carbamoyl chloride in the presence of an organic base to obtain a free base of rivastigmine.

17 Claims, 2 Drawing Sheets

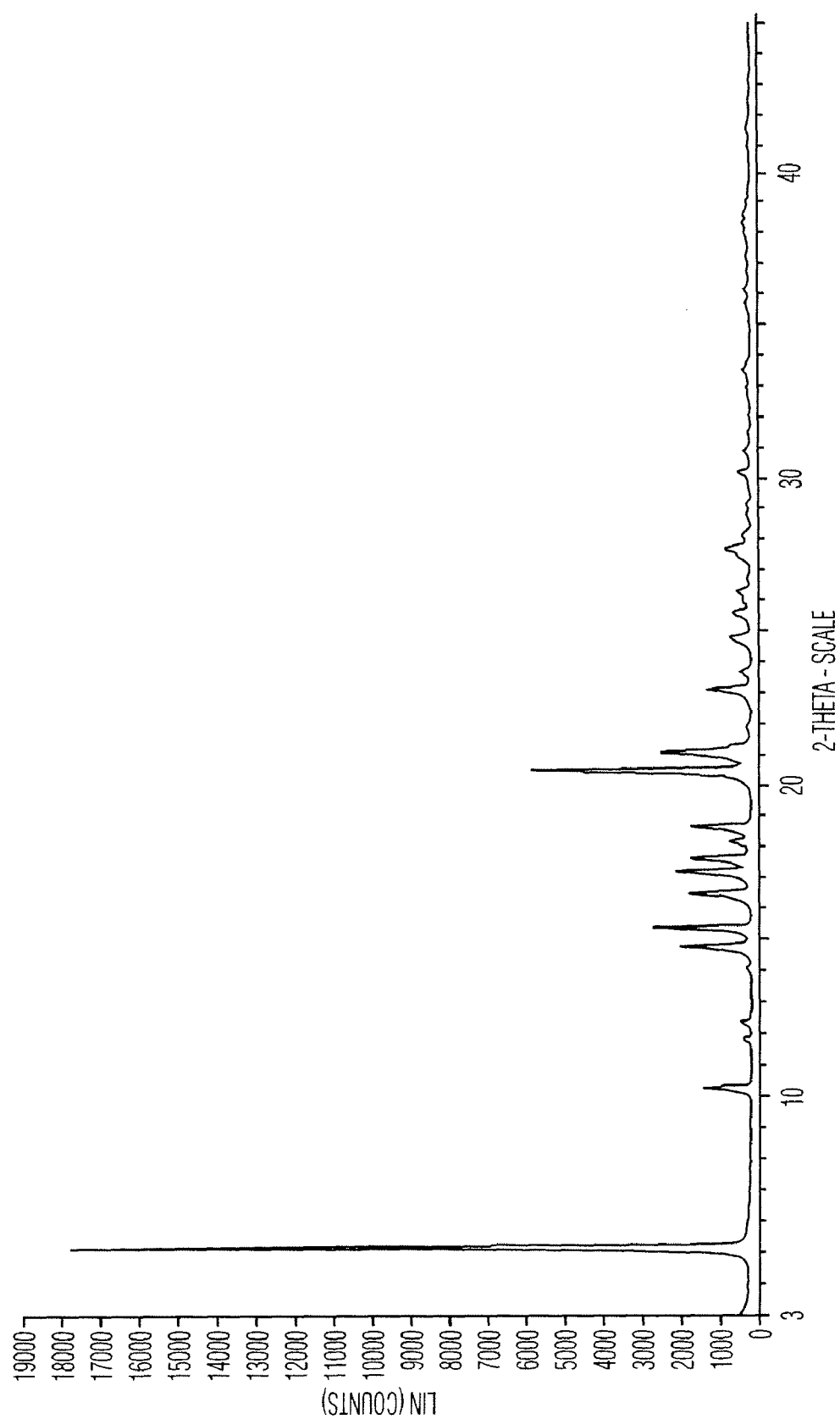

PREPARATION OF RIVASTIGMINE AND ITS SALTS

TECHNICAL FIELD

The present patent application relates to an improved process for the preparation of rivastigmine and its salts.

BACKGROUND

Rivastigmine hydrogen tartrate is chemically known as (S)—N-Ethyl-N-methyl-3-[1-(dimethylamino) ethyl]-phenyl carbamate hydrogen-(2R, 3R)-tartrate (hereinafter referred to as "rivastigmine tartrate") and has structural Formula I.

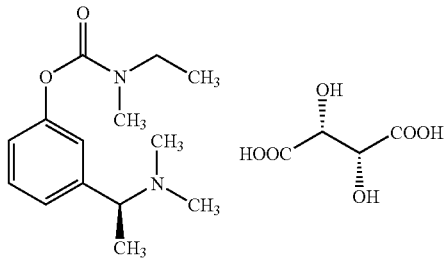

Formula I

Rivastigmine hydrogen tartrate is administered for the inhibition of reversible cholinesterase and is marketed under the brand name EXELON™ as capsules containing 0.5, 3, 4.5 and 6 mg rivastigmine base equivalent.

U.S. Pat. No. 4,948,807 describes the compound N-ethyl, N-methyl-3-[1-(dimethylamino)ethyl]phenyl carbamate and its pharmacologically acceptable salts along with a pharmaceutical composition useful for treating anticholinesterase activity in humans.

U.S. Pat. No. 5,602,176 describes (S)—N-ethyl-3-[(1-dimethylamino)ethyl]-N-methyl-phenyl carbamate in free base or acid addition salt form as useful for its anticholinesterase activity.

International Application Publication No. WO 2004/037771 A1 and European Patent 193926 describe a process for the preparation of (S)-3-[1-(dimethylamino)-ethyl]-phenyl-N-ethyl-N-methyl carbamate by the reaction of optically active m-hydroxyphenylethyl dimethylamine with a carbamoylhalide International application No. WO 2005/058804A1 describes a process for the preparation of rivastigmine by stereoselective reduction.

Consequently, it would be a contribution to the art to provide a process for the preparation of rivastigmine and its salts, which would be environment-friendly and suitable for commercial manufacturing.

SUMMARY

In one aspect, the present application provides a process for the preparation of rivastigmine or a pharmaceutically acceptable salt thereof, the process including the steps of:

i) reacting S-(−)-[1-(3-hydroxyphenyl)ethyl]dimethylamine of Formula III with N-ethyl-N-methyl carbamoyl chloride in the presence of an organic base to afford (S)—N-ethyl-N-methyl-3-[1-(dimethylamino)-ethyl]-phenyl carbamate (rivastigmine) of Formula II; and

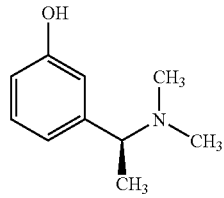

Formula III

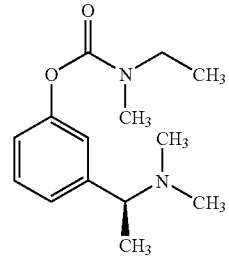

Formula II ii) reacting rivastigmine of Formula II with a pharmaceutically acceptable acid.

Each step is contemplated separately and in the context of the sequence.

In another aspect, the present application provides a process for the preparation of rivastigmine or a pharmaceutically acceptable salt thereof, the process including the steps of:

i) reacting S-(−)-[1-(3-hydroxyphenyl)ethyl]dimethylamine of Formula III with less than one molar equivalent of N-ethyl-N-methyl carbamoyl chloride in the presence of a base to afford rivastigmine of Formula II; and ii) reacting rivastigmine of Formula II with a pharmaceutically acceptable acid.

Each step is contemplated separately and in the context of the sequence.

In another aspect, the present application provides a process for preparation of S-(−)-[1-(3-hydroxyphenyl)ethyl]dimethylamine of Formula III, the process including the steps of:

a) reacting 1-(3-methoxy-phenyl)-ethylamine of Formula VI with L (+) mandelic acid to form diasteromeric salt of Formula V;

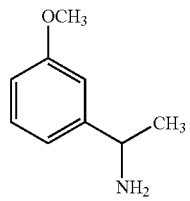

Formula VI

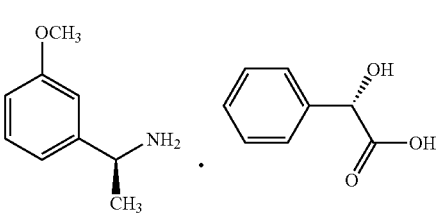

Formula V b) reacting the diasteromeric salt of Formula V with formic acid and formaldehyde to obtain S-(-)-1-(3-methoxy-phenyl)-ethyl amine of Formula IV; and

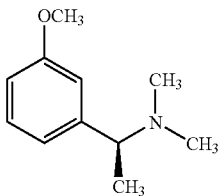

Formula IV c) reacting S-(-)-1-(3-methoxy phenyl)ethyl amine of Formula IV with aqueous hydrobromic acid.

In another aspect, the present application provides a process for preparation of 1-(3-methoxyphenyl)ethylamine of Formula VI that includes the steps of:

a) reacting 3-hydroxy acetophenone of Formula IX with dimethyl sulphate in the presence of potassium carbonate to give 1-(3-methoxyphenyl)ethanone of Formula VIII;

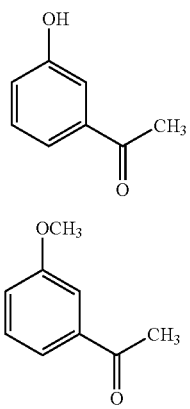

Formula IX

Formula VIII b) reacting 1-(3-methoxyphenyl)ethanone of Formula VIII with a reagent which is a source of ammonia and with a reducing agent.

In yet another aspect, the application provides a process for preparation of [1-(3-methoxyphenyl)ethyl] dimethyl amine of Formula VI comprising reacting R-(-)-[1-(3-methoxyphenyl)ethyl] dimethyl amine with a base having a highly ionic counter ion in a solvent medium that includes a polar aprotic solvent.

BRIEF DESCRIPTION OF THE DRAWINGS

FIG. 2 is X-ray power diffraction ("XRPD") pattern of rivastigimine hydrogen tartrate obtained in example 6.

DETAILED DESCRIPTION

Figure 1:
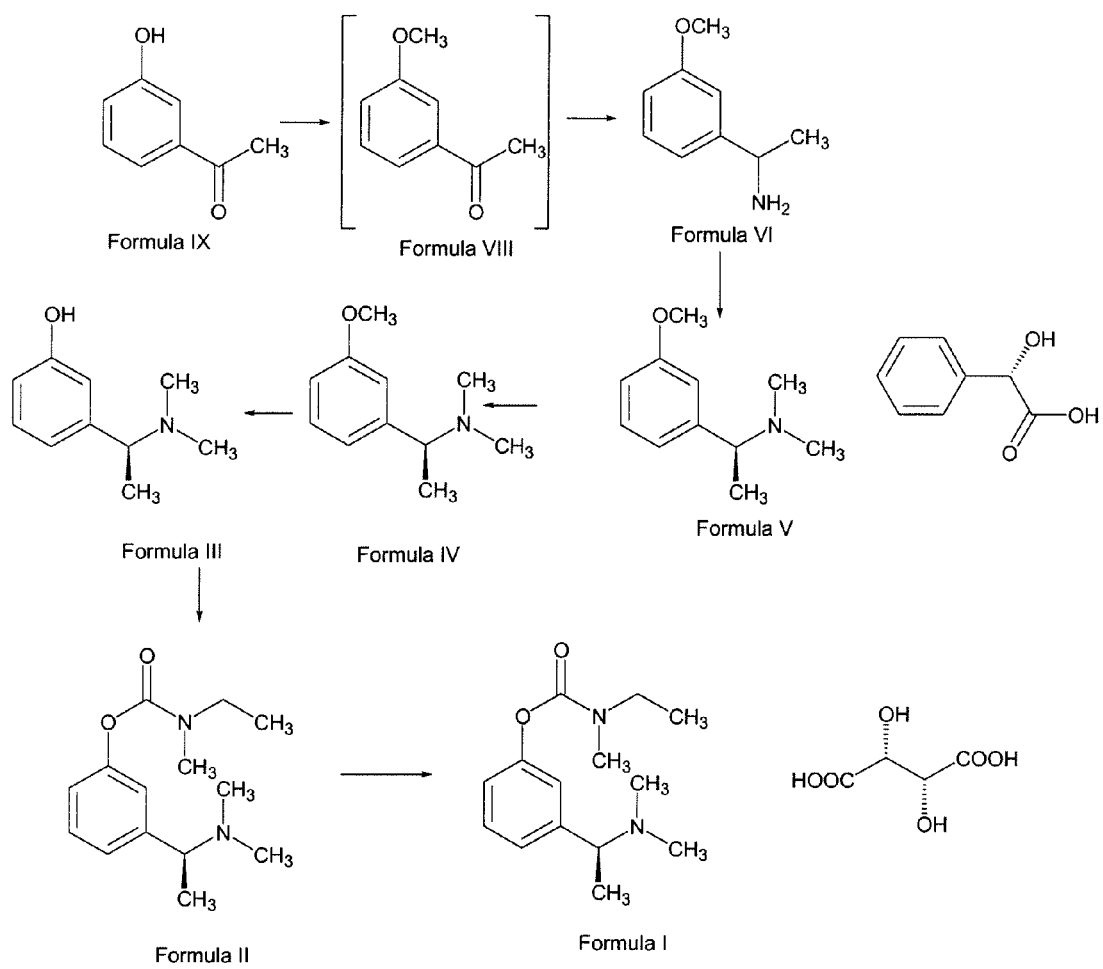
FIG. 1 is a schematic representation of a process for the preparation of rivastigmine hydrogen tartrate of Formula I.

The present patent application relates to an improved process for the preparation of rivastigmine and salts thereof.

In one aspect, the present application relates to a process for the preparation of rivastigmine or a pharmaceutically acceptable salt thereof that includes the steps of:

i) reacting S-(-)-[1-(3-hydroxyphenyl)ethyl]dimethylamine of Formula III with N-ethyl-N-methyl carbamoyl chloride in the presence of an organic base to afford (S)—N-ethyl-N-methyl-3-[1-(dimethylamino)-ethyl]-phenyl-carbamate (rivastigmine) of Formula II; and

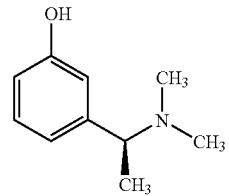

Formula III

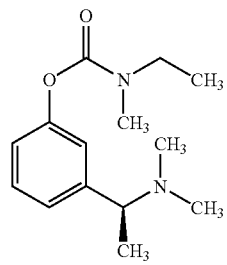

Formula II ii) reacting rivastigmine of Formula II with pharmaceutically acceptable acid.

Suitable organic bases that may be used in step i) include, but are not limited to, pyridine, lutidine, triethylamine, dimethylaminopyridine (DMAP), dicyclohexylamine, diisopropylethylamine and the like. Preferable organic base is pyridine In one variant, the reaction of step a) may be carried out in the presence of phase transfer catalyst. Suitable phase transfer catalyst includes but is not limited to tetra butyl ammonium bromide, methyltrioctylammonium chloride, crown ether, potassium bromide, potassium iodide, magnesium bromide, lithium bromide, preferably, tetra butyl ammonium bromide.

Suitable organic solvents that may be used in step a) include alcohols such as methanol, ethanol, isopropyl alcohol, n-butanol; ketones such as acetone, methyl isobutyl ketone, methyl ethyl ketone, n-butanone; halogenated solvents such as dichloromethane, ethylene dichloride, chloroform; esters such as ethyl acetate, n-propyl acetate, isopropyl acetate; hydrocarbon solvents such as toluene, xylene, n-hexane, n-heptane, cyclohexane; ethers such as 1,4-dioxane, tetrahydrofuran or mixtures thereof in various proportions.

The molar ratio of S-(-)-[1-(3-hydroxyphenyl)ethyl]dimethylamine of Formula III to N-ethyl-N-methyl carbamoyl chloride may range from about 1:0.5 to about 1:1.5, preferably about 1:0.9.

Suitable temperatures for conducting the reaction may range from about 15° C. to about 100° C., preferably from about 25° C. to about 35° C. The reaction can be conducted till the completion of the reaction. Typically the reaction time varies from about 1 hour to about 20 hours.

If desired, the rivastigmine thus obtained may be purified by converting into its acid addition salts, using acids such as hydrochloric acid, oxalic acid, hydrobromic acid, acetic acid, formic acid and the like, in a suitable solvent.

Suitable solvents which may be used for salt formation include but are not limited to: C2-C5 ketones such as acetone, ethyl methyl ketone, butanone and the like; alcohols such as ethanol, methanol, and isopropanol; ethers such as tetrahydrofuran, 1,4-dioxane, ethyl acetate, cyclohexane, n-hexane, diethyl ether and the like; water; and mixtures thereof.

The product may be further dried. Drying can be carried out in a tray dryer, vacuum oven, air oven, fluidized bed drier, spin flash dryer at temperatures of about 35° C. to about 70° C. with or without vacuum.

Step ii) involves reacting rivastigmine of Formula II with pharmaceutically acceptable acid.

Suitable pharmaceutically acceptable acids include hydrobromic acid, hydrochloric acid, and organic acids, such as acetic acid, succinic acid, oxalic acid, tartaric acid, formic acid, and maleic acid. Preferable acid is tartaric acid.

Suitable organic solvents that may be used include, but are not limited to: alcohols such as methanol, ethanol, isopropyl alcohol, n-butanol; ketones such as acetone, methyl isobutyl ketone, methyl ethyl ketone, and n-butanone; esters such as ethyl acetate, n-propyl acetate, and isopropyl acetate; hydrocarbon solvents such as toluene, xylene, n-hexane, n-heptane, and cyclohexane; and ethers such as 1,4-dioxane, and tetrahydrofuran. Mixtures of any of these solvents are also contemplated or their combinations without limitation.

The product may be further dried. Drying may be carried out in a tray dryer, vacuum oven, air oven, fluidized bed drier, spin flash dryer, flash dryer and the like. The drying can be carried out at temperatures of about 35° C. to about 70° C. with or without vacuum. The drying can be carried out for any desired time periods to achieve the desired product purity, times from about 1 to 20 hours frequently being appropriate.

The process described herein is believed to yield substantially pure rivastigmine tartrate.

Rivastigmine or any of the pharmaceutically acceptable salts of rivastigmine prepared in accordance with the process of the present application contains less than about 0.5%, or less than about 0.1%, by weight of the process related impurities.

The $D_{10}$, and $D_{90}$ values are useful ways for indicating a particle size distribution. $D_{90}$ refers to at least 90 volume percent of the particles having a size smaller than the said value. Likewise $D_{10}$ refers to 10 volume percent of the particles having a size smaller than the said value. $D_{50}$ refers to at least 50 volume percent of the particles having a size smaller than the said value. Methods for determining $D_{10}$, $D_{50}$ and $D_{90}$ include laser diffraction using Malvern equipment.

Rivastigmine tartrate prepared according to the present application has a $D_{10}$ less than 20 μm or less than 5 μm; $D_{50}$ less than 50 μm or less than 20 μm; and $D_{90}$ less than 150 μm or less than 50 μm. There is no specific lower limit for any of the D values.

Rivastigmine tartrate prepared according to the present application has untapped bulk density greater than about 0.10 g/ml, particularly about to 0.2 g/ml, and tapped bulk density greater than about 2 g/ml, particularly about 0.30 g/ml.

As referred to here in the term "bulk density untapped" is the weight of the sample divided by its non-packed volume and the term "bulk density tapped" is the weight of the sample divided by its packed volume. The units of bulk density are grams (g) per cubic centimeter (cc) or grams per milliliter. A powder having low bulk density will be lightweight and have greater surface area. A powder with high density will be much more compact and dense, exist as harder particles and will result in a more flow able product compared to powder with low bulk density Rivastigmine tartrate prepared according to the present application has residual solvents such as acetone less than 700 ppm; ethyl acetate less than 200 ppm; toluene less than 100 ppm; and each of isopropyl alcohol, n-Heptane, dichloromethane, methyl isobutyl ketone, pyridine less than 20 ppm.

In another aspect, the present application relates to a process for the preparation of rivastigmine or a pharmaceutically acceptable salt thereof that includes the steps of:

i) reacting S-(−)-[1-(3-hydroxyphenyl)ethyl]dimethylamine of Formula III with less than one molar equivalent of N-ethyl-N-methyl carbamoyl chloride in the presence of a base to afford rivastigmine of Formula II; and ii) reacting rivastigmine of Formula II with pharmaceutically acceptable acid.

Suitable bases that can be used in step i) include, but are not limited to, inorganic bases such as alkali metal hydrides, hydroxides, alkoxides and carbonates; organic bases such as pyridine, lutidine, triethylamine, DMAP, dicyclohexylamine, diisopropylethylamine and the like. Preferable base is pyridine In one variant of the process, the reaction of step a) may be carried out in the presence of a phase transfer catalyst. Suitable phase transfer catalysts include but are not limited to tetra butyl ammonium bromide, methyltrioctylammonium chloride, crown ether, potassium bromide, potassium iodide, magnesium bromide, and lithium bromide. Tetra butyl ammonium bromide is preferred.

Suitable organic solvents that may be used in step a) include alcohols such as methanol, ethanol, isopropyl alcohol, n-butanol; ketones such as acetone, methyl isobutyl ketone, methyl ethyl ketone, n-butanone; halogenated solvents such as dichloromethane, ethylene dichloride, chloroform; esters such as ethyl acetate, n-propyl acetate, isopropyl acetate; hydrocarbon solvents such as toluene, xylene, n-hexane, n-heptane, cyclohexane; ethers such as 1,4-dioxane, tetrahydrofuran or mixtures thereof in various proportions.

Suitable temperatures for conducting the reaction can range from about 15° C. to about 100° C., preferably from about 25° C. to about 35° C. The reaction can be conducted till the completion of the reaction. Typically the reaction time varies from about 1 hour to about 20 hours.

Rivastigmine can be purified by converting the free base into its acid addition salt in presence of suitable solvent preferably hydrochloride in isopropyl alcohol and converting back to free base.

The product may be further dried. Drying may be carried out in a tray dryer, vacuum oven, air oven, fluidized bed drier, spin flash dryer at temperatures of about 35° C. to about 70° C. with or without vacuum.

Step ii) involves reacting rivastigmine of Formula II with a pharmaceutically acceptable acid.

Suitable pharmaceutically acceptable acids include hydrobromic acid, hydrochloric acid, and organic acids, such as acetic acid, succinic acid, oxalic acid, tartaric acid, formic acid, and maleic acid. Preferable acid is tartaric acid.

Suitable organic solvents that may be used include, but are not limited to: alcohols such as methanol, ethanol, isopropyl alcohol, and n-butanol; ketones such as acetone, methyl isobutyl ketone, methyl ethyl ketone, and n-butanone; esters such as ethyl acetate, n-propyl acetate, and isopropyl acetate; hydrocarbon solvents such as toluene, xylene, n-hexane, n-heptane, and cyclohexane; and ethers such as 1,4-dioxane, and tetrahydrofuran. Mixtures of any of these solvents are also contemplated or their combinations with water in various proportions without limitation.

The product may be further dried. Drying may be suitably carried out in a tray dryer, vacuum oven, air oven, fluidized bed drier, spin flash dryer, flash dryer and the like. The drying can be carried out at temperatures of about 35° C. to about 70° C. with or without vacuum. The drying can be carried out for any desired time periods to achieve the desired product purity, times from about 1 to 20 hours frequently being appropriate.

In another aspect, the present application relates to a process for preparation of S-(−)-[1-(3-hydroxyphenyl)ethyl] dimethylamine of Formula III that includes the steps of:

a) reacting 1-(3-methoxy-phenyl)-ethylamine of Formula VI with L (+) mandelic acid to form diasteromeric salt of Formula V;

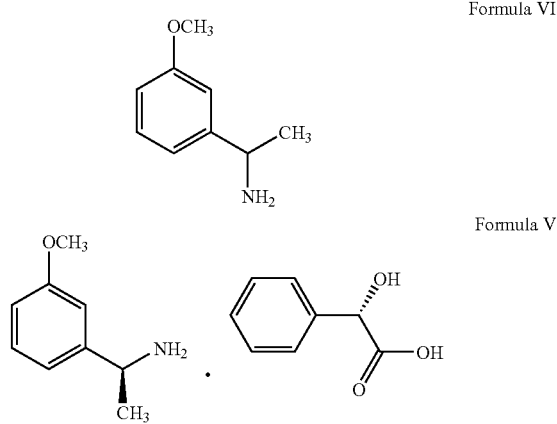

Formula VI

Formula V b) reacting the diasteromeric salt Formula V with formic acid and formaldehyde to obtain S-(−)-1-(3-methoxy-phenyl)-ethyl amine of Formula IV; and

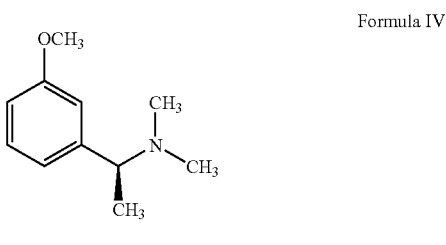

Formula IV c) reacting S-(−)-1-(3-methoxy phenyl)ethyl amine of Formula IV with aqueous hydrobromic acid.

Step a) involves reacting 1-(3-methoxy-phenyl)-ethylamine of Formula VI with L (+) mandelic acid in isopropyl alcohol to form diasteromeric salt of Formula V.

Suitable solvent for conducting the reaction other than isopropyl alcohol includes alcoholic solvents such as methanol, ethanol, propanol and the like. Suitable temperatures for conducting the reaction can range from about 30° C. to about 120° C.

The diastereomeric salt of Formula V is isolated from the final mixture by suitable techniques such as filtration by gravity, or by suction, centrifugation, and the like.

The reaction can be carried out for any desired time periods to achieve the desired product yield and purity, times from about 1 to 20 hours, or longer, frequently being adequate.

The wet cake obtained in the above step may optionally be further dried. Drying can be suitably carried out in a tray dryer, vacuum oven, air oven, fluidized bed drier, spin flash dryer, at temperatures of about 35° C. to about 70° C.

Step b) involves reacting the diasteromeric salt Formula V with formic acid and formaldehyde to obtain S-(−)-1-(3-methoxy-phenyl)-ethyl amine of Formula IV.

The diasteromeric salt of Formula V can be converted to free base and may be utilized in the reaction.

The obtained diastereomeric salt of S-(−)-[1-(3-methoxyphenyl)ethyl] dimethyl amine can be converted into free base involves adjusting the pH of the reaction solution to basic medium.

Suitable aqueous bases include but are not limited to organic bases such as methylamine, dimethylamine, triethylamine, ethyldi-isopropylamine, butylamine and the like; inorganic bases such as sodium hydroxide, potassium hydroxide, sodium carbonate, potassium carbonate, sodium bicarbonate, potassium bicarbonate and the like.

Suitable temperatures for this reaction can ranger from about 80 to 110° C. preferably about 95 to 100° C.

The obtained product may be recovered from the reaction solution by the conventional techniques.

Step c) involves reaction S-(−)-1-(3-methoxy-phenyl)-ethyl amine of Formula IVI with aqueous hydrobromic acid.

Suitably about 40% w/v to about 48% w/v aqueous hydrobromic acid is used for the reaction and suitable temperature for this reaction may range from about 90° C. to about 120° C.

Optionally, other reagents which may be used in this reaction includes but not limited to hydrogen iodide, potassium iodide, hydrochloric acid, potassium bromide, lithium bromide or mixtures thereof.

In another aspect, the present application relates to a process for preparation of 1-(3-methoxyphenyl)ethylamine of Formula VI that includes the steps of:

a) reacting 3-hydroxy acetophenone of Formula IX with dimethyl sulphate in the presence of potassium carbonate to give 1-(3-methoxyphenyl)ethanone of Formula VIII;

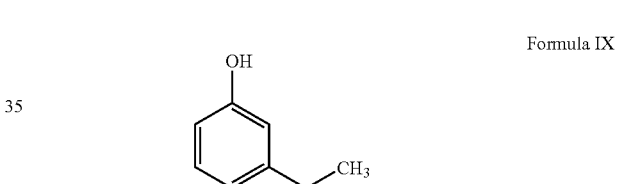

Formula IX

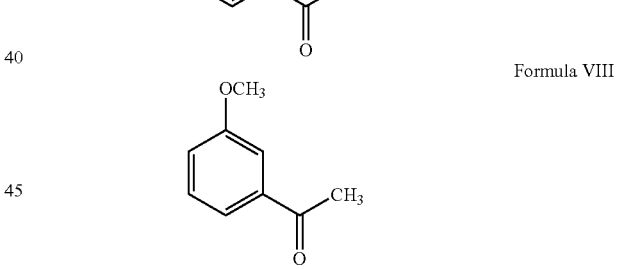

Formula VIII b) reacting 1-(3-methoxyphenyl)ethanone of Formula VIII with a reagent which is a source of ammonia and with a reducing agent.

Step a) involves reacting 3-hydroxy acetophenone of Formula IX with dimethyl sulphate in presence of potassium carbonate to give 1-(3-methoxyphenyl)ethanone of Formula VIII.

Suitable temperatures for conducting the reaction of step a) range from about 25° C. to about 75° C. preferably reflux temperature of the solvent used. The reaction may be carried out until completion of the reaction. Typically the reaction time varies from about 1 hour to about 10 hours.

Step b) involves reacting 1-(3-methoxyphenyl)ethanone of Formula VIII with a reagent which is a source of ammonia and with a reducing agent.

Suitable reagents which is a source of ammonia that may be used include but are not limited to ammonia, methanolic ammonia, hydroxylamine or combinations including ammonium formate in combination with methanolic HCl, ammonium formate in combination with isopropyl alcohol HCl, ammonium formate in combination with aqueous HCl, ammonium formate in combination with formic acid, formamide in combination with formic acid, formamide in combination with formic acid and isopropyl alcohol HCl, formamide in combination with formic acid and methanolic HCl, formamide in combination with formic acid and aqueous HCl.

Suitable reducing agents that may be used include but are not limited to chemical reducing agents such as sodium borohydride, lithium aluminium hydride, hydrogenation catalysts such as palladium, nickel and the like in combination with hydrogen.

The reaction of step b) may be carried out first by amination followed by reduction. Alternatively, simultaneous reductive amination is also contemplated.

The reaction between 1-(3-methoxyphenyl)ethanone of Formula VIII and the source of ammonia produces an aminated intermediate, which is then reduced. The term "aminated intermediate" denotes, for the purposes of this application only, nitrogen-containing compounds, including amines and imines, such as, for example, compounds of the Formulas (VIIa), (VIIb), and (VIIc) described herein below.

In one embodiment, ammonium formate is used to form the intermediate compound N-[1-(3-Methoxy-phenyl)-ethyl]-formamide of Formula VIIa in the reaction mixture, which may or may not be isolated. It is then converted to 1-(3-methoxyphenyl)ethylamine of Formula VI using isopropyl alcohol HCl.

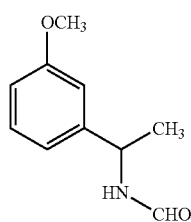

Formula VIIa

In another embodiment, hydrogenation with methanolic ammonia and raney nickel is used to form, as the intermediate compound 1-(3-methoxy phenyl)-ethanone oxime of Formula VIIb in the reaction mixture, which may or may not be isolated.

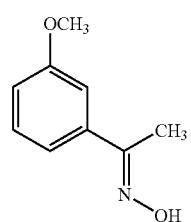

Formula VIIb

In another embodiment, hydroxylamine hydrochloride is used to form the intermediate compound 1-(3-methoxyphenyl)ethanamine of Formula VIIc in the reaction mixture, which may or may not be isolated. It is converted to 1-(3-methoxyphenyl)ethylamine of Formula VI by hydrogenation using raney nickel.

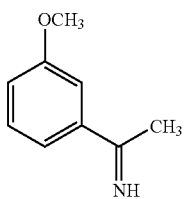

Formula VIIc

Suitable solvent that may be used include, but are not limited to, alcohols such as methanol, ethanol, isopropyl alcohol, n-butanol; ketones such as acetone, methyl isobutyl ketone, methyl ethyl ketone, n-butanone; halogenated solvents such as dichloromethane, ethylene dichloride, chloroform; esters such as ethyl acetate, n-propyl acetate, isopropyl acetate; hydrocarbon solvents such as toluene, xylene, n-hexane, n-heptane, cyclohexane; ethers such as 1,4-dioxane, tetrahydrofuran; aprotic polar solvents such as N,N-dimethylformamide (DMF), dimethylsulfoxide (DMSO), dimethylacetamide (DMA).

Suitable temperatures for conducting the reaction may range from about 25° C. to about 200° C., preferably reflux temperature of the solvent used.

In yet another aspect the application also provides a process for preparation of [1-(3-methoxyphenyl)ethyl] dimethyl amine of Formula VI comprising reacting R-(−)-[1-(3-methoxyphenyl)ethyl] dimethyl amine with a base having a highly ionic counter ion in a solvent medium comprising polar aprotic solvent.

Suitable organic solvents used in this reaction includes but not limited to aprotic polar solvents such as DMF, dimethyl acetamide, N-1,3-dimethyl-2-imidazolinone, DMSO.

Suitable base with highly ionic counter ion include $C_1$-$C_6$ alkyl lithium compounds, optionally condensed with $C_1$-$C_6$ straight chain, branched or cyclic alkyl amines such as methyl lithium, Sec-butyl lithium and n-butyl lithium and like, metal hydroxides such as potassium hydroxide, sodium hydroxide, lithium hydroxide and like Suitable temperatures for conducting the reaction may range from about 30 to about 180° C.; preferably reflux temperature of the solvent used.

The resultant [1-(3-methoxyphenyl)ethyl] dimethyl amine of Formula VI can be used directly for the preparation of rivastigmine or a salt thereof using the process describe in the present application or by any process that may be know in the art.

Having thus described the invention with reference to particular preferred embodiments and illustrative example, those in the art may appreciate modification to the invention as described and illustrated that do not depart from the spirit and scope of the invention as disclosed in the specification. The examples are set for the to aid in understanding the invention but are not intended to, and should not be construed to, limit its scope in any way. The examples do not include detailed descriptions of conventional methods. Such methods are well know to those of ordinary skill in the art and are described in numerous publications. All references mentioned herein are incorporated in their entirety.

EXAMPLES

Example 1

Preparation of 1-(3-Methoxy Phenyl) Ethyl Amine (Formula VI)

To a solution of 200 g of 3-hydroxyacetophenone of Formula IX in 400 ml of acetone, 244 g of potassium carbonate were charged and stirred for about 10 minutes. To the above reaction mixture 204 g of dimethyl sulphate was added for about 60 minutes followed by heating to about 45° C. and stirred for about 1 hour. After completion of the reaction, the reaction mixture was quenched by charging of 800 ml of water. Organic and aqueous layers were separated and 370 g of ammonium formate was added to the organic layer. The contents were then heated to about 180° C. and stirred for about 2 hours. The reaction mixture was then cooled to about 30° C. and 600 ml of water was charged. The mixture was extracted with ethyl acetate (1×400 ml, 2×150 ml). The organic layers were combined and charged 600 ml of hydrogen chloride in isopropanol (18% w/w) followed by heating to about 75° C. and stirred for about 3 hours. The mixtures was distilled completely at about 65° C. under vacuum and again charge 100 ml ethyl acetate and distilled completely at about 65° C. to afford residue.

600 ml of ethyl acetate was charged to the residue and stirred for 30 minutes. Filtered the solid and was washed with 200 ml of ethyl acetate. The wet solid was then charged into 600 ml of water and pH was adjusted to about 11 by addition of 68.8 ml of 40% aqueous sodium hydroxide. The reaction mixture was extracted with ethyl acetate (1×200 ml, 2×100 ml). Organic and aqueous layers were separated and the organic layer was distilled off completely at about 65° C. under vacuum to afford 128 g of the title compound.

HPLC purity: 99.1%

Example 2

Preparation of S-(−)-1-(3-Methoxy Phenyl) Ethyl Amine Mandalate (Formula V)

To a solution of 40 g of 1-(3-methoxyphenyl)ethyl amine of Formula VI in 1400 ml of isopropyl alcohol, 41.2 g of L-(+)-mandelic acid was added and stirred for about 15 minutes. The mixture was heated to about 75° C. and stirred for about 45 minutes followed by cooling to about 37° C. and stirred for about 10 minutes. The separated solid was filtered and the solid was washed 80 ml of isopropyl alcohol. The solid obtained was suck dried for 3 hours to obtain the wet compound of the diasteromeric salt of Formula V.

The obtained diasteromeric salt of Formula V was charged into a clean and dry round bottom flask containing 480 ml of isopropyl alcohol followed by heating to reflux. The resultant solution was stirred at reflux for about 45 minutes followed by cooling to about 37° C. and stirred for about 10 minutes. Solid was separated by filtration and the solid was washed with 20 ml of isopropyl alcohol. The solid obtained was dried at about 55° C. for about 2 hours to yield 29 g of the title compound.

Purity by chiral HPLC: 99.9%.

Example 3

Preparation of S-(−)-[1-(3-Methoxyphenyl) Ethyl] Dimethyl Amine (Formula IV)

To a solution of 200 g of S-(−)-1-(3-methoxyphenyl)ethyl amine L (+)-Mandalate (diasteromeric salt) of Formula V in 800 ml of water, charged 148 g of formaldehyde (40%), 182.1 g of formic acid (98%) and the contents were heated to about 100° C. The resultant mixture was stirred at about 100° C. for about 5 hours. After the completion of the reaction, the mixture was cooled to about 30° C. and washed with toluene (3×1000 ml). Aqueous layer pH was adjusted to 10.5 using 160 ml of 40% aqueous sodium hydroxide solution and extracted with ethyl acetate (2×500 ml). The organic layers were combined and washed with water (2×400 ml). The organic layer was distilled completely at about 60° C. under vacuum to yield 108 g of the title compound.

Purity by HPLC: 98.15%.

Example 4

Preparation of S-(−)-[1-(3-Hydroxyphenyl) Ethyl] Dimethyl Amine (Formula III)

50 g of S-(−)-[1-(3-methoxyphenyl)ethyl] dimethyl amine of Formula IV and 283 g of 48% aqueous HBr solution were charged into a clean and round bottom flask followed by heating to about 110° C. and stirred for about 6 hours. After completion of the reaction, the mixture was cooled to about 30° C. and charged 250 ml of water and pH was adjusted to about 10.5 using 162 ml caustic lye and the reaction mixture was extracted with ethyl acetate ((1×150 ml, 2×50 ml)). The organic layer thus obtained was washed with water (2×50 ml) and treated with activated charcoal. The organic layer is filtered through celite and washed with 100 ml of ethyl acetate. The filtrate was distilled completely at below 60° C. under vacuum. To the residue charged 200 ml of n-heptane at about 50° C. and stirred for about 90 minutes at about 25° C. The separated solid was filtered and washed the solid with n-heptane 50 ml and suck dried. The solid obtained was dried at about 50° C. for about 5 hours to yield 41.5 g of the title compound.

Purity by HPLC: 99.07%.

Example 5

Preparation of (S)—N-Ethyl-N-Methyl-3-[1-Dimethyl-Amino)-Ethyl]-Phenyl Carbamate (Formula II)

6 kg of S-(−)-[1-(3-hydroxyphenyl)ethyl] dimethyl amine of Formula III and 12 L of Methyl Isobutyl Ketone(MIBK) were charged and stirred for about 10 minutes. To this reaction solution 3.44 kg of pyridine, 1.18 kg of tetrabutylammonium bromide were charged and stirred for about 15 minutes to form clear solution. 3.97 kg of N-ethyl, N-methyl carbomyl chloride was added to the reaction mixture for about 30 minutes. Heated the contents to about 30° C. and stirred for about 15 hours. After completion of the reaction 48 lit of water was charged and pH was adjusted to about 1.5 using 3.72 lit of 36% aqueous hydrochloric acid. Stirred the contents for about 30 minutes at about 25° C. and aqueous layer was separated. The aqueous layers were then washed with MIBK (2×12 lit) and separate the aqueous layer. Aqueous layer pH was adjusted to 12.5 using 6 lit of 40% aqueous sodium hydroxide solution and stirred for about 15 minutes. The aqueous layer was then extracted with MIBK (2×12 lit) and separated the organic layer. Washed the organic layer with water (2×12 lit) and separated the organic layer. The obtained organic layer was distilled off completely at about 60° C. to afford residue.

To the obtained residue 48 lit of ethyl acetate was added and pH of the reaction solution was adjusted to about 2 by adding about 6 lit of 18% hydrochloride in isopropyl alcohol at about 5° C. and stirred for about 90 minutes for solid separation. The separated solid was filtered and washed with 6 lit of ethyl acetate. The obtained wet solid was again charged into a reaction containing 30 lit of water and adjusted the pH to about 12.5 using 1.8 lit of 40% aqueous sodium hydroxide solution (caustic lye). The reaction mass was extracted with MIBK (2×12 lit) and the combined organic layer was washed with water (2×12 lit). The organic layer was distilled completely at about 60° C. to afford residue.

To the obtained residue 48 lit of ethyl acetate was added and pH of the reaction solution was adjusted to about 2 by adding about 6 lit of 18% hydrochloride in isopropyl alcohol at about 5° C. and stirred for about 90 minutes for solid separation. The separated solid was filtered and washed with 6 lit of ethyl acetate. The obtained wet solid was again charged into a reaction containing 30 lit of water and adjusted the pH to about 12.5 using 1.8 lit of 40% aqueous sodium hydroxide solution. The reaction mass was extracted with MIBK (2×12 lit) and the combined organic layer was washed with water (2×12 lit). The organic layer was distilled completely at about 60° C. to afford the title compound.

Purity by HPLC. 99.33%

Example 6

Preparation of Rivastigmine Tartrate (Formula I)

3 kg of rivastigmine freebase of Formula II in 105 lit of acetone, 1.8 kg of L-(+)-Tartaric acid was charged and heated to about 60° C. followed by stirring for about 30 minutes for complete dissolution. The resulting reaction solutions was passed through celite and wash the bed with 13.5 lit acetone to made particle free. The obtained clear solution was distilled off up to 50% of the initial volume and cooled to 30° C. 12 g of rivastigmine hydrogen tartrate was added and stirred for about 60 minutes. The reaction mixture was heated to reflux and stirred for about 60 minutes and cooled to about 30° C. and stirred for about 60 minutes for solid separation. The separated solid was filtered and washed the solid with 3 lit of acetone. Solid obtained was dried at about 60° C. for about 9 hours to afford 4.10 kg of the title compound.

Purity by HPLC: 97.37%.

Example 7

Conversion of R-(−)-[1-(3-Methoxyphenyl) Ethyl] Dimethyl Amine into its Racemic Mixture of Formula VI 100 g of R-(−)-[1-(3-methoxyphenyl)ethyl] dimethyl amine mandelic acid salt, 500 ml water was charged and stirred for about 15 minutes. pH of the reaction solution was a adjusted to 10 by addition of 40% aqueous sodium hydroxide solution and stirred for about 20 minutes. 500 ml ethyl acetate was added to the reaction solution and stirred for about 10 minutes and separated the organic and aqueous layer. The obtained organic layer was distilled off completely under vacuum to get 48.8 g of the residue.

2 g of the above obtained residue containing R-(−)-[1-(3-methoxyphenyl)ethyl] dimethyl amine, 0.5 g of sodium hydroxide and 10 ml of dimethyl sulfoxide were charged in a clean and dry round bottom flask and stirred for about 15 minutes. The reaction mixture was heated to about 90° C. and maintained for about 2 hours followed by cooling to room temperature. 50 ml of water were added to the above reaction mixture and stirred for about 45 minutes. To the resultant reaction solution 15 ml dichloromethane was added and stirred for about 15 minutes and separated the organic layer. The obtained organic layer was distilled off completely under vacuum below 45° to 1.3 g of 1-(3-methoxyphenyl)ethyl] dimethyl amine of Formula VI.

Entiomeric ratio by chiral HPLC: 49.93:50.07

Example 8

Alternate Preparation of 1-(3-Methoxyphenyl) Ethyl Amine (Formula VI)

To a solution of 300 g of 3-methoxyacetophenone of Formula VII in 1000 ml of 10.9% ammonia in methanol, 300 g of Raney nickel in 100 ml of methanol (Raney nickel was prewashed with 2×150 ml of methanol to remove moisture) was charged, followed by heating to about 90° C. The resultant suspension was agitated at about 90° C. under 4 kg/cm$^2$ anhydrous hydrogen gas pressure for about 45 hours. After completion of the reaction, the reaction mass was cooled to about 30° C. and the suspension was filtered through a celite bed, followed by washing the celite with 300 ml of methanol. The filtrate was distilled completely at about 55° C. under vacuum. To the residue, 300 ml of acetone was charged and distilled completely. To the residue, 900 ml of acetone was charged and dry HCl gas was passed at about 0° C. until the pH of the mass was less than 1. The resultant suspension was stirred at about 5° C. for about 3 hours. Solid was separated by filtration and the solid was washed with 100 ml of acetone. The solid obtained was dried at 50° C. for about 5 hours. The above solid is charged in a 4 neck round bottom flask and stirred for about 10 minutes and PH is adjusted to about 11.0 using 65 ml of caustic lye and extracted with 3×200 ml of dichloromethane. The obtained organic layer is distilled completely distilled at about 45° C. to afford 179.6 g of title compound.

Example 9

Alternate Process for the Preparation of 1-(3-Methoxy-Phenyl)-Ethyl Amine (Formula VI)

To a solution of 50 g of 3-methoxy acetophenone in 250 ml of isopropyl alcohol charged 92 g of potassium carbonate and 46 g of hydroxylamine hydrochloride followed by heating the contents to about 60° C. and maintained for about 2 hours. The reaction mass is cooled to about 28° C., filtered the separated solid and washed with 100 ml of isopropyl alcohol. The resulting filterate was distilled under vacuum at about 55° C. to yield 58 g of 1-(3-methoxy-phenyl)-ethanone oxime.

To a solution of 45 g of 1-(3-methoxy-phenyl)-ethanone oxime in 675 ml of methanol charged 45 g of Raney Ni. The resultant suspension was agitated at about 28° C. under 3 kg/cm$^2$ anhydrous hydrogen gas pressure for about 4 hours. After completion of the reaction, the reaction mass was filtered through celite and washed with 90 ml of methanol. The filterate was distilled under vacuum at about 55° C. To the residue charged 150 ml of methanolic HCL and distilled completely under vacuum at about 50° C. To the residue charged 100 ml of acetone and stirred at about 15° C. for about one hour. Separated solid was filtered and the solid was washed with 30 ml of acetone. The solid obtained was dried at about 50° C. for about 3 hours.

The dried solid was charged into a clean and dry 4 neck round bottom flask containing 150 ml of water and stirred for about 20 minutes. pH was adjusted to 11.0 using 30 ml of caustic lye and stirred for about 20 minutes. It is then extracted with 3×50 ml of di chloro methane and the combined di chloro methane layer was distilled at about 42° C. to afford 21.0 g of the title compound.

Purity by HPLC: 99.1%.

The invention claimed is:

1. A process for preparing rivastigmine or a salt thereof comprising reacting S-(−)-[1-(3-hydroxyphenyl)ethyl]dimethylamine with N-ethyl-N-methyl carbamoyl chloride in the presence of an organic base to obtain a free base of rivastigmine, wherein the organic base is pyridine, lutidine, triethylamine, dimethylaminopyridine (DMAP), dicyclohexylamine, or diisopropylethylamine.

2. The process of claim 1, wherein the organic base is pyridine.

3. The process of claim 1, wherein the reaction is carried out in the presence of a phase transfer catalyst.

4. The process of claim 3, wherein the phase transfer catalyst is tetrabutyl ammonium bromide, methyltrioctylammonium chloride, or a crown ether.

5. The process of claim 3, wherein the phase transfer catalyst is tetrabutyl ammonium bromide.

6. The process of claim 1, wherein the reaction is carried out in a solvent medium comprising $C_3$-$C_8$ ketone.

7. The process of claim 6, wherein said solvent medium comprises methyl isobutyl ketone.

8. The process of claim 1, further comprising converting said free base of rivastigmine to rivastigmine tartrate.

9. A process for preparing rivastigmine or a salt thereof comprising reacting S-(−)-[1-(3-hydroxyphenyl)ethyl]dimethylamine with less than one molar equivalent of N-ethyl-N-methyl carbamoyl chloride.

10. The process of claim 9, wherein the reaction is carried out in the presence of a base.

11. The process of claim 10, wherein the base is pyridine.

12. The process of claim 9, wherein the reaction is carried out in the presence of a phase transfer catalyst.

13. The process of claim 12, wherein the phase transfer catalyst is tetrabutyl ammonium bromide.

14. The process of claim 9, wherein the reaction is carried out in a solvent medium comprising C3-C8 ketone.

15. The process of claim 14, wherein solvent medium comprises methyl isobutyl ketone.

16. The process of claim 9, further comprising reacting rivastigmine free base with tartaric acid to afford rivastigmine tartrate.

17. The process of claim 1, wherein S-(−)-[1-(3-hydroxyphenyl)ethyl]dimethylamine is prepared by:
    a) reacting 1-(3-methoxy-phenyl)-ethylamine with optically pure mandelic acid to form a salt;
    b) reacting the salt of step a) with formic acid and formaldehyde to obtain S-(−)-1-(3-methoxy-phenyl)-ethyl amine; and
    c) reacting S-(−)-1-(3-methoxy-phenyl)-ethyl amine with aqueous hydrobromic acid to afford S-(−)-[1-(3-hydroxyphenyl)ethyl]dimethylamine.

* * * * *